(12) United States Patent
Hashimoto et al.

(10) Patent No.: US 11,039,895 B2
(45) Date of Patent: Jun. 22, 2021

(54) INDUSTRIAL REMOTE CONTROL ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 342 days.

(21) Appl. No.: 15/755,121

(22) PCT Filed: May 27, 2016

(86) PCT No.: PCT/JP2016/002576
§ 371 (c)(1),
(2) Date: Feb. 26, 2018

(87) PCT Pub. No.: WO2017/033352
PCT Pub. Date: Mar. 2, 2017

(65) Prior Publication Data
US 2018/0243920 A1    Aug. 30, 2018

(30) Foreign Application Priority Data
Aug. 25, 2015  (JP) .............................. JP2015-165479

(51) Int. Cl.
*G05B 19/18* (2006.01)
*G05B 19/04* (2006.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ... B25J 3/00; B25J 9/163; B25J 9/1664; B25J 9/1692; B25J 13/00; B25J 19/04;
(Continued)

(56) References Cited

U.S. PATENT DOCUMENTS

| 5,937,143 A | 8/1999 | Watanabe et al. |
| 8,513,560 B2 * | 8/2013 | Takahashi ............. B23K 11/115 219/86.25 |

(Continued)

FOREIGN PATENT DOCUMENTS

| JP | S59-135507 A | 8/1984 |
| JP | S62-049403 A | 3/1987 |

(Continued)

OTHER PUBLICATIONS

JP2007061924_ABSTRACT_ENGLISH: Abstract of Foreign Reference "JP2007061924" is translated into English (EPO Machine Translation) (Year: 2007).*

(Continued)

*Primary Examiner* — B M M Hannan
(74) *Attorney, Agent, or Firm* — Oliff PLC

(57) ABSTRACT

Remote control robot system includes a master device, slave arm having plurality of control modes including automatic and manual mode, control device configured to operate slave arm, an entering-person sensing device configured to detect entering person into operational area of slave arm, entering-person identifying information acquisition device configured to acquire entering-person identifying information for identifying whether entering person is operator who carries master device, and operation regulating device configured to regulate operation of slave arm based on information acquired from entering-person sensing device and information acquisition device. In automatic mode, operation regulating device regulates operation of slave arm when entering (Continued)

person is detected. In manual mode, operation regulating device allows operation of slave arm to continue when entering person is detected and entering person is operator, and regulates operation of the slave arm when entering person is other than operator.

8 Claims, 4 Drawing Sheets

(51) Int. Cl.
| | |
|---|---|
| B25J 3/00 | (2006.01) |
| A61B 34/37 | (2016.01) |
| G05B 19/418 | (2006.01) |
| B25J 9/00 | (2006.01) |
| B25J 9/16 | (2006.01) |
| B23P 19/04 | (2006.01) |
| B25J 13/00 | (2006.01) |
| B25J 19/04 | (2006.01) |
| B25J 13/08 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/0081; B25J 9/1646; B25J 9/1653; B25J 9/1674; B25J 9/1612; B25J 19/028; B25J 9/1602; B25J 13/085; B25J 13/087; B25J 9/0084; B25J 9/1697; B25J 13/006; B25J 13/08; B25J 9/0087; B25J 9/1669; B25J 13/06; B25J 13/088; B25J 18/00; B25J 9/161; B25J 9/1682; B25J 9/1689; B25J 19/023; B25J 3/04; B25J 9/1633; B25J 9/1628; B25J 13/02; B25J 11/008; B25J 13/003; B25J 13/065; B25J 13/025; B25J 13/084; B25J 9/126; B25J 19/02; B25J 19/06; B25J 11/005; B25J 9/1661; G05B 19/409; G05B 19/42; G05B 2219/33056; G05B 2219/40202; G05B 19/4182; G05B 2219/40143; G05B 2219/39004; G05B 2219/40182; G05B 2219/40145; G05B 2219/40387; G05B 2219/40139; G05B 2219/40161; G05B 2219/40146; G05B 2219/40627; G05B 2219/39439; G05B 2219/40022; G05B 2219/39531; G05B 2219/40163; G05B 2219/39533; G05B 2219/35464; G05B 2219/40142; G05B 2219/33007; G05B 2219/40169; G05B 2219/40183; G05B 2219/40134; G05B 2219/40195; G05B 2219/40162; G05B 2219/40136; G05B 2219/37297; G05B 2219/39102; Y10S 901/03; Y10S 901/41; Y10S 901/10; Y10S 901/46; Y10S 901/02; Y10S 901/09; Y10S 901/47; Y10S 901/08; Y10S 901/27; G06T 7/62; G06T 7/70; G06F 3/017; B23Q 15/12; H04N 5/23219; H04N 7/181; B23P 19/04; B23P 21/002; B23P 21/00
USPC .................................. 700/245, 250, 253, 257
See application file for complete search history.

(56) References Cited

U.S. PATENT DOCUMENTS

| | | | |
|---|---|---|---|
| 2004/0061466 A1* | 4/2004 | Hashimoto | ............... F16P 3/12 318/445 |
| 2004/0186627 A1* | 9/2004 | Watanabe | ............ G05B 19/425 700/264 |

(56) References Cited

U.S. PATENT DOCUMENTS

| | | | | |
|---|---|---|---|---|
| 2004/0260426 | A1* | 12/2004 | Johannessen | B25J 19/06 700/245 |
| 2007/0096674 | A1* | 5/2007 | Hashimoto | B25J 9/1674 318/568.13 |
| 2007/0293987 | A1* | 12/2007 | Yamada | B25J 19/023 700/245 |
| 2008/0125908 | A1* | 5/2008 | Sjoberg | B25J 9/1674 700/247 |
| 2009/0058342 | A1* | 3/2009 | Nihei | B25J 9/1674 318/568.24 |
| 2009/0128079 | A1 | 5/2009 | Sjoberg | |
| 2009/0177307 | A1* | 7/2009 | Miyazaki | B25J 9/1674 700/110 |
| 2010/0191372 | A1* | 7/2010 | Nihei | B25J 9/1676 700/245 |
| 2010/0286826 | A1* | 11/2010 | Tsusaka | B25J 9/1633 700/254 |
| 2011/0208355 | A1* | 8/2011 | Tsusaka | B25J 9/1664 700/246 |
| 2011/0295399 | A1* | 12/2011 | Plociennik | B22D 41/52 700/97 |
| 2012/0043831 | A1* | 2/2012 | Sakakibara | B25J 19/06 307/326 |
| 2012/0296471 | A1* | 11/2012 | Inaba | B25J 9/163 700/253 |
| 2013/0245824 | A1* | 9/2013 | Barajas | B25J 9/1664 700/253 |
| 2016/0271800 | A1* | 9/2016 | Stubbs | B25J 9/1666 |
| 2017/0197310 | A1* | 7/2017 | Aurnhammer | B25J 9/1664 |

FOREIGN PATENT DOCUMENTS

| | | |
|---|---|---|
| JP | H07-194609 A | 8/1995 |
| JP | H09-085655 A | 3/1997 |
| JP | H09-272096 A | 10/1997 |
| JP | 2003-311661 A | 11/2003 |
| JP | 2007-61924 A | 3/2007 |

OTHER PUBLICATIONS

JP2007061924A.English: Specification of Foreign Reference "JP2007061924" is translated into English (EPO Machine Translation) (Year: 2007).*

JP2007061924A_drawing.english.partially: Drawings of Foreign Reference "JP2007061924" is Translated into English partially (EPO Machine Translation) (Year: 2007).*

Aug. 16, 2016 Search Report issued in International Patent Application No. PCT/JP2016/002576.

Feb. 27, 2018 International Preliminary Report on Patentability issued in International Patent Application No. PCT/JP2016/002576.

Mar. 23, 2017 Office Action issued in Taiwan Patent Application No. 105126749.

* cited by examiner

INDUSTRIAL REMOTE CONTROL ROBOT SYSTEM

TECHNICAL FIELD

The present disclosure relates to an industrial remote control robot system provided with a master device and a slave arm.

BACKGROUND ART

Conventionally, remote control robot systems provided with a master device and a slave arm which operates according to manipulation of the master device are known. As the master device, a manipulator, a control lever, a manual operation button, etc. may be used. In such remote control robot systems, some are configured so that the posture of the slave arm follows the posture of the manipulator as the master device. Patent Document 1 discloses this kind of art.

In Patent Document 1, a master-slave type manipulator for medical use, which is provided with a portable arm manipulating part as the master device is disclosed. This portable arm manipulating part includes an operation table with a shoulder belt for an operator, a display provided to the operation table, and a plurality of small master arms provided to the operation table. Tip-end parts of these master operation arms are provided with gripping forceps corresponding to gripping forceps provided to tip-end parts of surgical tools which are manipulated by the master arms, respectively.

REFERENCE DOCUMENT OF CONVENTIONAL ART

Patent Document

[Patent Document 1] JP1995-194609A

DESCRIPTION OF THE DISCLOSURE

Problems to be Solved by the Disclosure

The manipulator for medical use disclosed in Patent Document 1, the forceps attached to the manipulator and its hand parts operate, and its operating speed is slow and its operating range is narrow, as compared with industrial robots. Therefore, in the manipulator for medical use, even if the operator who manipulates the master device and the manipulator are close to each other, the operator's safety is not impaired. However, in an industrial robot, when a person enters unprepared into an operational area of the robot, there is a possibility that a person and a robot may collide. Thus, while the industrial robot is operating, when a person enters into the operational area of the robot (e.g., inside of a safety fence), the robot performs an emergency stop.

Though, also in the industrial remote control robot system, a situation may occur, in which the operator approaches the slave arm, and operates the master device while checking the operation of the slave arm is suitable. Therefore, the present disclosure proposes an art which enables an operator to manipulate a master device within an operational area of a slave arm in an industrial remote control robot system.

SUMMARY OF THE DISCLOSURE

According to one aspect of the present disclosure, a remote control robot system includes a master device configured to receive manipulation of an operator, a slave arm having a plurality of control modes including an automatic mode in which the slave arm is operated based on a prestored task program, and a manual mode in which the slave arm is operated based on the operator's manipulation received by the master device, a control device configured to operate the slave arm in one selected from the plurality of control modes, an entering-person sensing device configured to detect an entering person into an operational area of the slave arm, an entering-person identifying information acquisition device configured to acquire entering-person identifying information for identifying whether the entering person is the operator who carries the master device, and an operation regulating device configured to regulate the operation of the slave arm based on the information acquired from the entering-person sensing device and the entering-person identifying information acquisition device. While the slave arm is in the automatic mode, the operation regulating device regulates the operation of the slave arm when the entering person is detected. While the slave arm is the manual mode, the operation regulating device allows the operation of the slave arm to continue when the entering person is detected and the entering person is the operator, and regulates the operation of the slave arm when the entering person is other than the operator.

According to the industrial remote control robot system described above, the slave arm continues its operation even when the operator who carries the master device enters into the operational area of the slave arm. Therefore, the operator is able to manipulate the master device in the operational area of the slave arm. Normally, since the operator who carries the master device operates the master device while monitoring the motion of the slave arm, he/she can predict the motion of the slave arm, and operate the master device to avoid a collision with the slave arm.

Further, in the remote control robot system described above, when the slave arm operates in the automatic mode, the operation of the slave arm is regulated for any person entering into the operational area of the slave arm. Therefore, the collision of the person entering into the operational area with the slave arm is prevented.

Effect of the Disclosure

According to the industrial remote control robot system of the present disclosure, it enables the operator to manipulate the master device within the operational area of the slave arm.

MODES FOR CARRYING OUT THE DISCLOSURE

Hereinafter, one embodiment of the present disclosure is described reference to the accompanying drawings.

[Remote Control Robot System 100]

Figure 1:
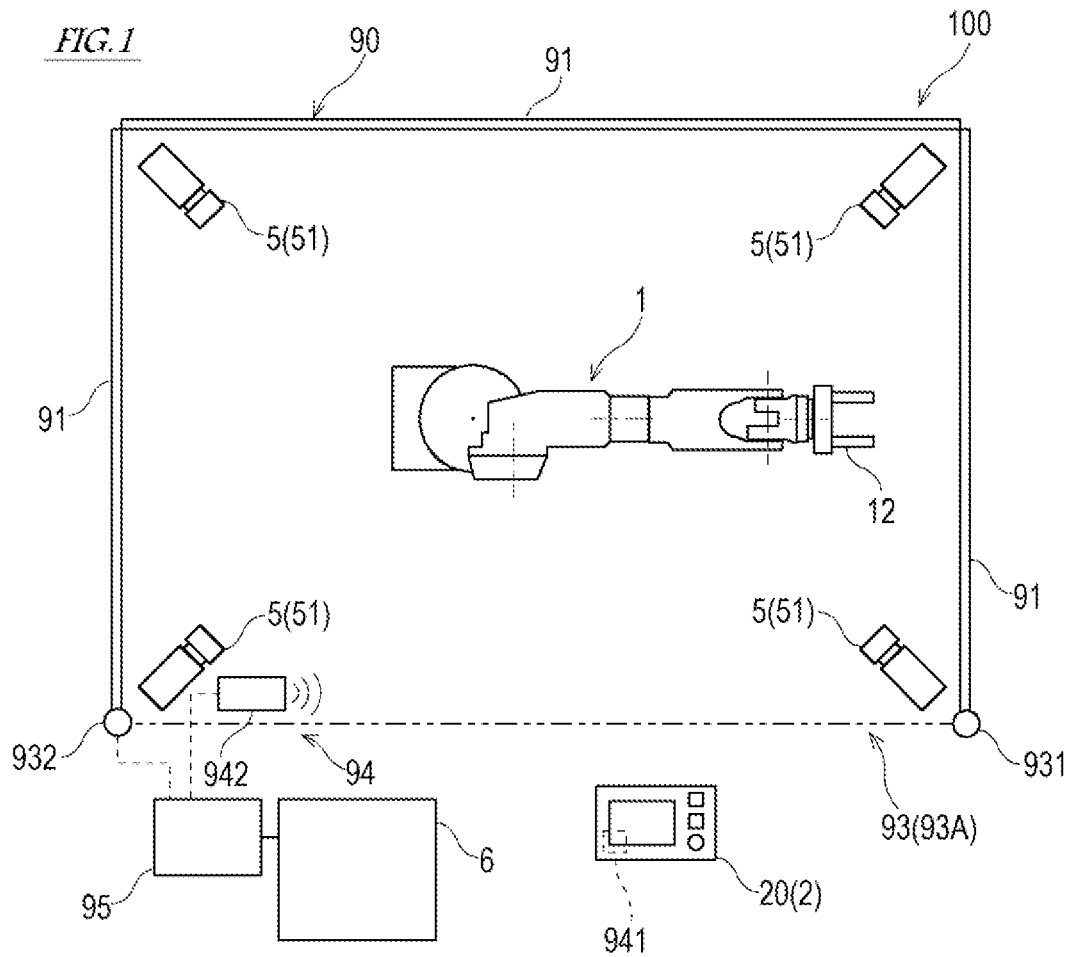
FIG. 1 is a plan view schematically illustrating a configuration of a remote control robot system according to one embodiment of the present disclosure.
Figure 2:
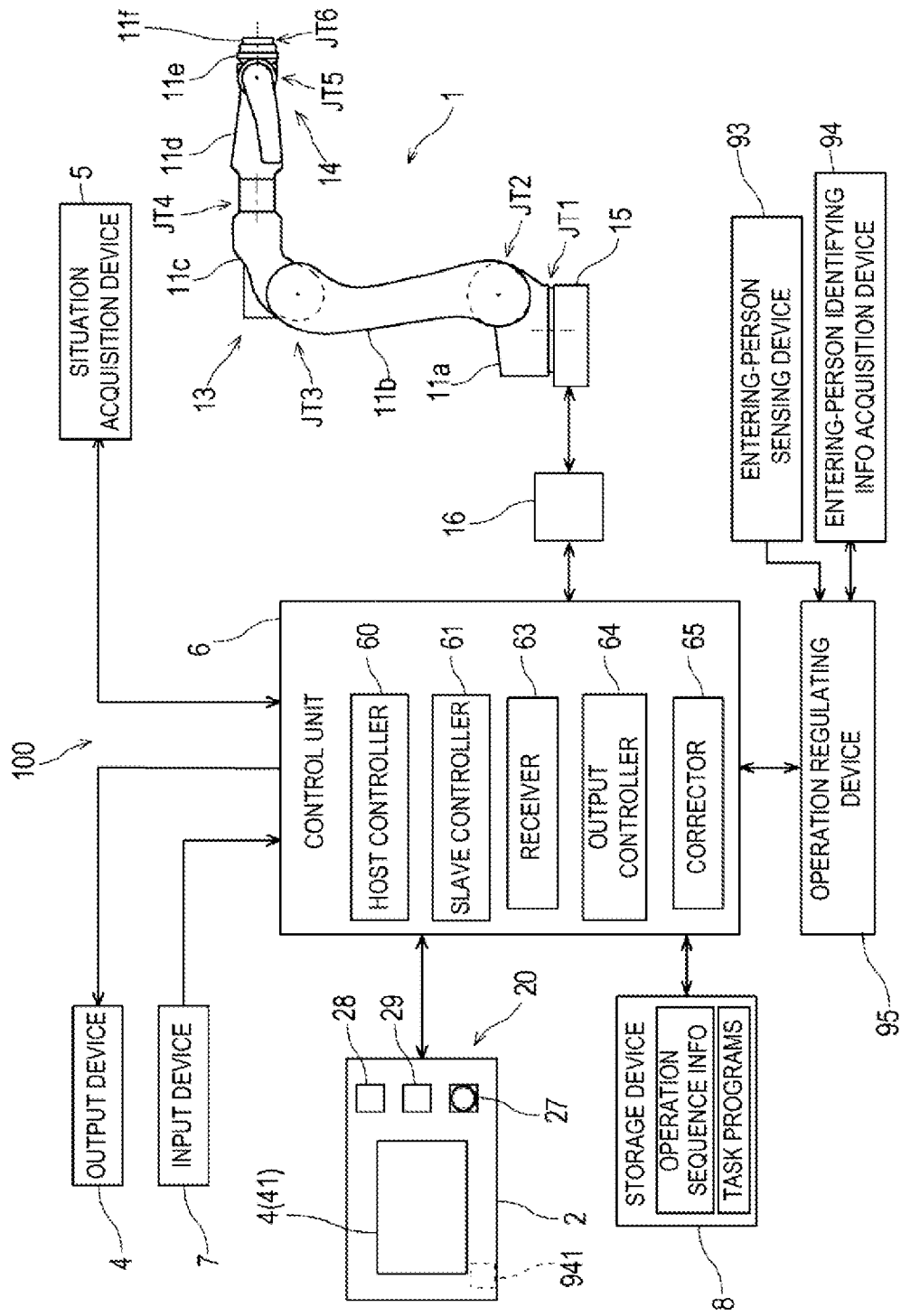
FIG. 2 is a block diagram illustrating a configuration of a control system of the remote control robot system.

FIG. 1 is a plan view schematically illustrating a configuration of a remote control robot system 100 according to one embodiment of the present disclosure, and FIG. 2 is a block diagram illustrating a configuration of a control system of the remote control robot system 100. As illustrated in FIGS. 1 and 2, the remote control robot system 100 is a master-slave type robot system, which includes a slave arm 1, a master device 20, an input device 7, an output device 4, a situation acquisition device 5, an entering-person sensing device 93, an entering-person identifying information acquisition device 94, an operation regulating device 95, and a control unit 6 which controls the system 100 comprehensively.

The slave arm 1 according to this embodiment has three control modes of an automatic mode, a manual mode, and a correctable automatic mode. The control mode of the slave arm 1 is switchable so that the operation of the slave arm 1 is controlled in one selected from the plurality of control modes.

A control mode in which the slave arm 1 is operated according to a preset task program is herein referred to as "the automatic mode." In the automatic mode, the slave arm 1 automatically performs a given work without operator's manipulation of the master device 20, similar to a conventional teaching playback robot.

Moreover, a control mode in which the slave arm 1 is operated based on the operator's manipulation received by the master device 20 is herein referred to as "the manual mode." The master device 20 is capable of receiving the operation inputted by the operator directly manipulating the master device 20. Note that, in the manual mode, the operator's manipulation received by the master device 20, and the motion of the slave arm 1 which operates based on the manipulation may be corrected automatically.

Moreover, a control mode in which the slave arm 1 is operated according to the preset task program while the operation is corrected as required by the operator's manipulation received by the master device 20 is herein referred to as "the correctable automatic mode." In the correctable automatic mode, the motion of the slave arm 1 which is operating according to the preset task program is corrected based on the operator's manipulation received by the master device 20.

Below, each component of the remote control robot system 100 is described in detail.

[Slave Arm 1]

As illustrated in FIG. 2, the slave arm 1 is an articulated robot arm having a plurality of joints JT1-JT6, which is comprised of a serially coupled body of a plurality of links 11a-11f, and a pedestal 15 which supports the coupled body. In more detail, at the first joint JT1, the pedestal 15 and a base-end part of the first link 11a are coupled to each other rotatably about an axis extending vertically. At the second joint JT2, a tip-end part of the first link 11a and a base-end part of the second link 11b are coupled to each other rotatably about an axis extending horizontally. At the third joint JT3, a tip-end part of the second link 11b and a base-end part of the third link 11c are coupled to each other rotatably about an axis extending horizontally. At the fourth joint JT4, a tip-end part of the third link 11c and a base-end part of the fourth link 11d are coupled to each other rotatably about an axis extending in the longitudinal directions of the fourth link 11d. At the fifth joint JT5, a tip-end part of the fourth link 11d and a base-end part of the fifth link 11e are coupled to each other rotatably about an axis perpendicular to the longitudinal directions of the fourth link 11d. At the sixth joint JT6, a tip-end part of the fifth link 11e and a base-end part of the sixth link 11f are twistably and rotatably coupled to each other. A mechanical interface is provided to a tip-end part of the sixth link 11f. An end effector 12 (see FIG. 1) corresponding to the contents of work is attached to the mechanical interface attachably and detachably.

Figure 3:
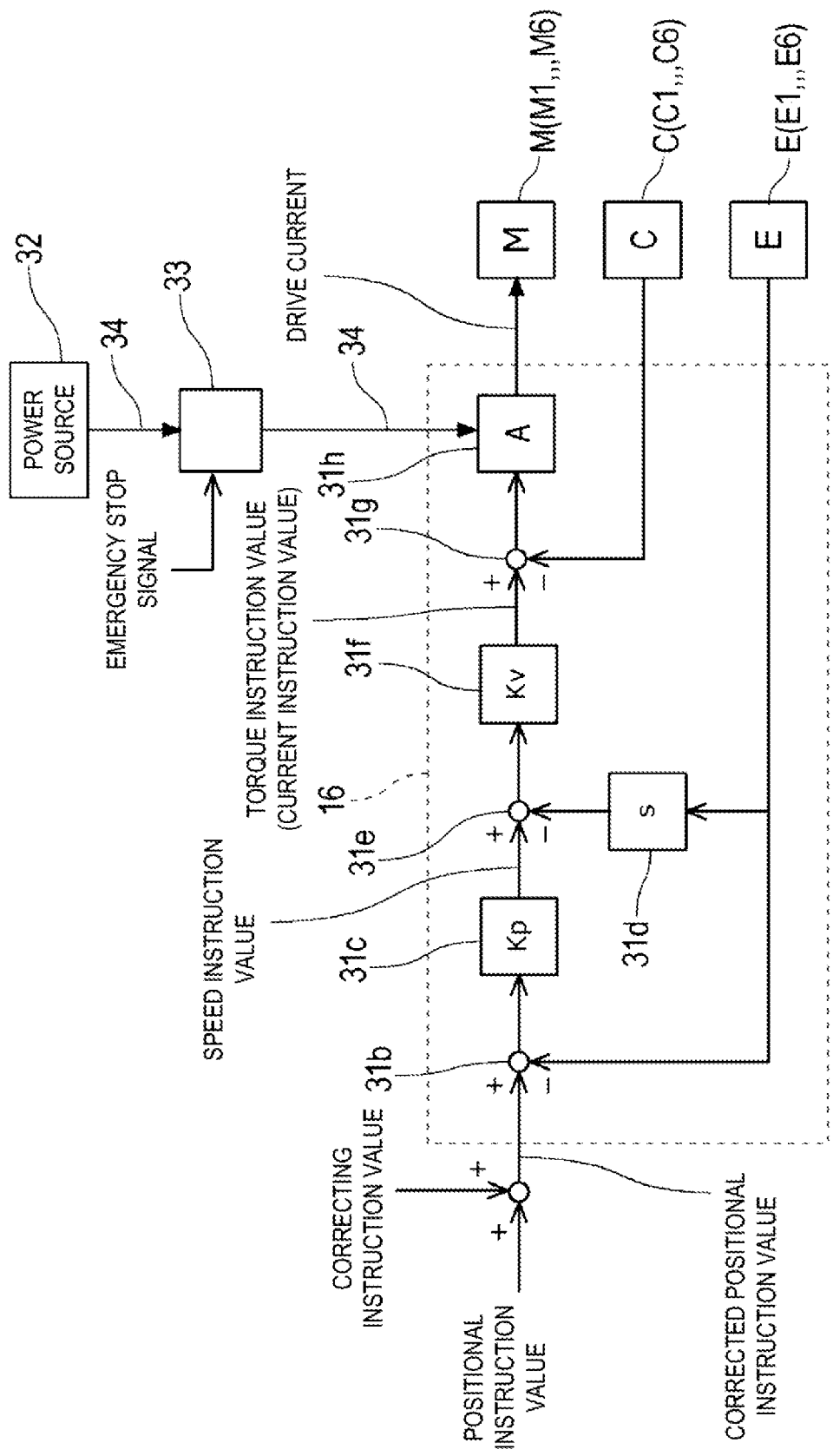
FIG. 3 is a block diagram illustrating a configuration of a control system of a slave arm.

FIG. 3 is a block diagram illustrating a configuration of a control system of the slave arm 1. In this figure, a concrete electric configuration focusing on a motor controller 16 is illustrated. As illustrated in FIG. 3, the joints JT1-JT6 of the slave arm 1 are provided with drive motors M1-M6, respectively, each of which is one example of an actuator which relatively rotates two members connected by the joint. The drive motors M1-M6 are, for example, servo motors which are servo-controlled by the motor controller 16. Moreover, the drive motors M1-M6 are provided with position sensors E1-E6 which detect rotational positions thereof and current sensors C1-C6 which detect current for controlling the rotations. The position sensors E1-E6 may be, for example, encoders, resolvers, or pulse generators, which is capable of detecting the rotational positions. Note that, in the description of the drive motors M1-M6, the position sensors E1-E6, and the current sensors C1-C6, 1-6 of the suffixes are given to the alphabet corresponding to the respective joints JT1-JT6. Below, when an arbitrary joint is illustrated among the joints JT1-JT6, the suffix is omitted and the joint is referred to as "JT," and the same is applied to the drive motor M, the position sensor E, and the current sensor C.

The drive motor M, the position sensor E, and the current sensor C are electrically connected with the motor controller 16. Although the motor controller 16 according to this embodiment is capable of servo-controlling the plurality of the drive motors M alone, the motor controllers 16 may be provided corresponding to the respective drive motors M.

Electric power is supplied from a power source 32 to the motor controller 16 through a power supply path 34. A connector 33 which switches between supplying of the electric power from the power source 32 to the motor controller 16 and intercepting of the supply, is provided to the power supply path 34. The connector 33 becomes in an open state in response to an emergency stop signal from the control unit 6 to intercept the power supply from the power source 32 to the motor controller 16.

The motor controller 16 generates a drive instruction value (a current instruction value) based on a positional instruction value acquired from the control unit 6 (in detail, a slave controller 61) described later, a servo gain, etc., and supplies drive current corresponding to the drive instruction value to the drive motor M. An output rotational angle of the drive motor M is detected by the position sensor E, and is fed back to the motor controller 16. Note that the functions of the motor controller 16 and the slave controller 61 may be implemented by a single circuit or a single arithmetic device.

When the positional instruction value is inputted into the motor controller 16 from the control unit 6 (in detail, the slave controller 61), the inputted positional instruction value is given to the plus-side input of a subtractor 31b. A signal indicative of the rotational angle detected by the position sensor E (a present position value) is given to the minus-side input of the subtractor 31b. The subtractor 31b subtracts the rotational angle from the positional instruction value. The output of the subtractor 31b is given to a coefficient multiplier 31c, where the output is amplified by a position gain Kp, and it is given to the + input of a subtractor 31e. The resultant obtained by a differentiator 31d differentiating the rotational angle from the position sensor E is given to the − input of the subtractor 31e. The output of the subtractor 31e is given to a coefficient multiplier 31*f*, where the output is amplified by a speed gain Kv, and it is given to the + input of a subtractor 31*g*. The current value from the current sensor C is given to the − input of the subtractor 31*g*. The subtracted output of the subtractor 31*g* is inputted into an amplifier circuit 31*h* as the drive instruction value, and drive current corresponding to the amplified drive instruction value is supplied to the drive motor M.

[Master Device 20]

The master device 20 is a means for receiving the operator's manipulation. In the remote control robot system 100 according to this embodiment, a portable console 2 is used as the master device 20. The console 2 is provided with a joystick 27 which receives manipulations according to the position and posture of the slave arm 1. In this embodiment, although the joystick 27 is adopted as a manipulation tool which receives the manipulations according to the position and posture of the slave arm 1, a known manipulation tool, such as a manipulator, a touch panel, a key, a lever, a button, a switch, and a dial plate, may be used instead of the joystick 27.

The console 2 is provided with, as part of the input device 7, an emergency stop button 28 which receives an instruction for causing the slave arm 1 to forcibly perform an emergency stop, and a control mode changeover switch 29 which receives a changeover operation of the control mode of the slave arm 1. The console 2 may be also provided with other input devices 7 than those described above.

Moreover, a display device 41 and a speaker (not illustrated) are mounted to the console 2, as part of the output device 4.

The master device 20 is communicatably connected with the control unit 6 wirelessly. The master device 20 receives operator's operations of the various manipulation tools, and inputs the received operations into the control unit 6.

[Input Device 7]

The input device 7 is an input means which is installed outside the workspace together with the master device 20, and receives the operational instructions from the operator, and inputs the received operational instructions into the control unit 6. Into the input device 7, operations other than the manipulations according to the position and posture of the slave arm 1 are inputted. The input device 7 includes one or more operational input tools which input the operational instructions other than the position and posture of the slave arms 1, such as the control mode changeover switch 29 and the emergency stop button 28. The one or more operational input tools may include, for example, known operational input tools, such as a touch panel, a key, a lever, a button, a switch, and a dial plate. Moreover, a mobile terminal, such as a programmable display device (pendant) or a tablet computer, may be used as the input device 7.

[Situation Acquisition Device 5]

The situation acquisition device 5 is a means for acquiring situation indicative of a situation of the slave arm 1 in the workspace. The situation information includes information used in order to recognize the position, the posture and the like of the slave arm 1 in the workspace, or a situation around the slave arm 1. More specifically, the situation information includes, for example, information necessary to enable a recognition of the situation of the slave arm 1 and the situation around the slave arm 1 in the workspace, such as the position and posture of the slave arm 1 in the workspace, a spatial relationship between the slave arm 1 and a workpiece, or a spatial relationship between the slave arm 1 and an assembled component to which an assembling component is assembled.

The situation acquisition device 5 is implementable by, for example, a sensor, a camera device 51 (see FIG. 1), a communication device, an encoder, etc. The sensor includes, for example, a laser sensor, a radar sensor or the like which measures a distance or a position to a workpiece (the assembling component) or the assembled component. Further, it may also include a stereoscopic camera which is a sensor for measuring a distance from the slave arm 1 to an object around thereof by using image data obtained from a plurality of imaging devices. The communication device includes, for example, a communication device which acquires information from the assembling component or the assembled component, or from a sensor and an imaging device installed at a given position in the workspace. The encoder includes, for example, an encoder which is capable of detecting an amount of movement or the position of the slave arm 1.

The situation acquisition device 5 acquires situation information as required, and the acquired situation information is inputted into the control unit 6 described later, where it is used for a motion control of the slave arm 1. Further, the control unit 6 may also be configured to control the output device 4 to output the situation information. The situation acquisition device 5 may be attached to the slave arm 1, or may be attached at a suitable position in the workspace. Moreover, the number of situation acquisition devices 5 attached may be one, or may be plural. The attachment position and the attachment number are arbitrary, as long as a suitable number of situation acquisition devices 5 are attached at positions where the situation information can appropriately be acquired.

[Output Device 4]

The output device 4 outputs the information transmitted from the control unit 6. The output device 4 is installed at a position where the operator who is operating the master device 20 is able to easily and visually recognize the output device 4. The output device 4 includes at least the display device 41, and may further include a printer, a speaker, a hazard light, etc. The display device 41 displays and outputs the information transmitted from the control unit 6. For example, the speaker outputs the information transmitted from the control unit 6 as sound. Moreover, for example, the printer prints and outputs the information transmitted from the control unit 6 on recording media, such as paper.

[Storage Device 8]

The storage device 8 stores various task programs used for the control of the slave arm 1. The task program may be created as an operational flow for each work. The task program is created, for example, by teaching, and is stored in the storage device 8 so as to be associated with the identifying information of the slave arm 1 and the task. Note that, although the storage device 8 is illustrated independently from the control unit 6, a storage device provided to the control unit 6 may function as the storage device 8.

Moreover, the storage device 8 stores operation sequence information created beforehand. The operation sequence information is information related to the operation sequence which defines a series of work processes to be carried out by the slave arm 1 in the workspace. In the operation sequence information, the operation order of the work processes is associated with the control modes of the slave arm 1. Moreover, in the operation sequence information, each work process is associated with the task program for causing the slave arm 1 to automatically perform the work. Note that the operation sequence information may include a program for each work process to cause the slave arm 1 to automatically perform the work.

[Control Unit 6]

As illustrated in FIG. 2, the control unit 6 is communicatably connected with the slave arm 1, the master device 20, the output device 4, the situation acquisition device 5, the input device 7, the storage device 8, and the operation regulating device 95 by wiredly or wirelessly.

The control unit 6 is a so-called computer, and has an arithmetic processing part, such as a CPU, and a memory part, such as a ROM and/or a RAM (none of them is illustrated). The memory part stores control program to be executed by the control unit 6, various fixed data, etc. The arithmetic processing part performs, for example, transmission and reception of data with external devices, such as the input device 7, the output device 4, and the storage device 8. Moreover, the arithmetic processing part performs inputs of detection signals from various sensors, and outputs of control signals to respective controlled objects. In the control unit 6, the arithmetic processing part reads and executes software, such as the program stored in the memory part, to perform processing for controlling various operations of the system 100. Note that the control unit 6 may perform each processing by an centralized control with a single computer, or may perform each processing by a distributed control with a plurality of collaborating computers. Moreover, the control unit 6 may be comprised of a microcontroller, a programmable logic controller (PLC), etc.

The control unit 6 includes a host controller 60, a slave controller 61, a receiver 63, an output controller 64, and a corrector 65, as functional blocks. In FIG. 2, although these functional blocks are collectively illustrated as a single control unit 6, each functional block or combination(s) of a plurality of functional blocks may be implemented by one or more independent computers. In this case, some of the functional blocks may be disposed in the workspace, and the remainder may be disposed outside the workspace.

The slave controller 61 controls the operation of the slave arm 1. In the automatic mode, the slave controller 61 reads the task program stored in the storage device 8, generates the positional instruction value according to the task program, and gives the positional instruction value, a servo gain, etc. to the motor controller 16 of the slave arm 1. Moreover, in the manual mode, the slave controller 61 generates the positional instruction value based on the manipulating information accepted by the master device 20 and received by the receiver 63, and gives the positional instruction value, a servo gain, etc. to the motor controller 16 of the slave arm 1. Moreover, in the correctable automatic mode, the slave controller 61 reads the task program stored in the storage device 8, generates the positional instruction value (or the corrected positional instruction value) based on the task program and the correcting instruction value acquired from the corrector 65, and gives the positional instruction value, a servo gain, etc. to the motor controller 16 (see FIG. 3). Note that, in the correctable automatic mode, if the correcting instruction value is not given from the corrector 65, the correcting instruction value is calculated as zero.

The receiver 63 receives input signals transmitted from the outside of the control unit 6. The input signals received by the receiver 63 includes, for example, the signal transmitted from the console 2 which is the master device 20, the signal transmitted from the input device 7, the situation information transmitted from the situation acquisition device 5, etc.

The output controller 64 controls the output device 4 to output information of to be notified to the operator from the output device 4. For example, when starting a selected portion of the operation sequence, the output device 4 outputs to the display device 41 information which identifies a target slave arm 1, and information which urges an input of selection of the control mode of the slave arm 1. Moreover, for example, when the control mode of the slave arm 1 is the manual mode or the correctable automatic mode, the output device 4 outputs to the display device 41 the situation information and operating situation of the slave arm 1 which is manipulated by the master device 20. Moreover, for example, when a failure occurs to the system 100, the output device 4 outputs an alarm to the speaker or the display device 41.

The corrector 65 corrects, when the control mode of the slave arm 1 is the correctable automatic mode, the motion of the slave arm 1 based on the manipulation received by the master device 20. For example, when the position and posture of the joystick 27 change when the operator moves the joystick 27, the master device 20 receives displacements of the position and posture as correcting instructions, and inputs them into the control unit 6. When the control mode of the slave arm 1 is the correctable automatic mode and the receiver 63 receives the correcting instruction signal, the corrector 65 generates a correcting instruction value based on the correcting instruction signal. The equation or map to calculate the correcting instruction value from the correcting instruction signal is stored beforehand Such a correcting instruction value may be, for example, a value proportional to amounts of change in the position and posture of the joystick 27. The generated correcting instruction value is transmitted to the slave controller 61, and the corrected positional instruction value is outputted from the slave controller 61 to the motor controller 16 (see FIG. 3).

The host controller 60 reads the operation sequence information stored in the storage device 8, and outputs the instructions to the slave controller 61, the master controller 62, the output controller 64, and the corrector 65 so that the slave arm 1, the master device 20, the output device 4, and the situation acquisition device 5 operate in accordance with the operation sequence information.

[Operation of Remote Control Robot System 100]

Next, one example of operation of the remote control robot system 100 having the above configuration is described. Here, an operational flow of the system 100 is described for a case where the remote control robot system 100 is established as an automobile assembly line, and is applied to one example in which the slave arm 1 is made to perform a work to attach a seat to an automobile body. However, the remote control robot system 100 according to the present disclosure may be applied widely, not limited to such an automobile assembly line, to various production facilities.

The operation sequence information on the seat attachment work to the automobile body stored in the storage device 8 is comprised of a component extracting task T1 in which a seat is extracted from a container, a component carrying task T2 in which the seat is carried to near an attachment position of the body, and a component attaching task T3 in which the seat near the attachment position is attached to the attachment position, and these tasks T1-T3 are repeatedly performed in this order. The component extracting task T1 and the component carrying task T2 among this operation sequence are "automatic portions" in which the slave arm 1 operates in the automatic mode.

The automatic portion of the operation sequence is associated with the automatic mode as the control mode. Moreover, the component attaching task T3 of the operation sequence is the "selected portion" in which the slave arm 1 operates in the control mode selected from the automatic mode, the manual mode, and the correctable automatic mode. The selected portion of the operation sequence is not associated with a specific control mode, but the control mode is selectable.

First, the control unit 6 reads given operation sequence information stored in the storage device 8, and starts the control of the system 100 in accordance with the operation sequence information.

First, the control unit 6 reads the task program of the component extracting task T1 from the storage device 8 and executes it. Then, the control unit 6 reads and executes the task program of the component carrying task T2. In the component extracting task T1 and the component carrying task T2, the control unit 6 controls the operation of the slave arm 1 in the automatic mode.

Once the component carrying task T2 is finished, the control unit 6 displays on the display device 41 a selection screen for urging the operator the selection of the control mode of the subsequent component attaching task T3. At the same time, the control unit 6 causes the display device 41 to output the situation information of the slave arm 1 of which the control mode is going to be selected. Here, the situation information displayed on and outputted to the display device 41 may include the identifying information on the slave arm 1 currently displayed, the contents of the process to be performed subsequently, etc.

The operator visually recognizes the situation information of the slave arm 1 displayed on the display device 41, and selects one of the three control modes. The operator's selection of the control mode is received by the master device 20 or the input device 7, and is inputted into the control unit 6.

In the above, when the automatic mode is selected, the control unit 6 reads the task program of the component attaching task T3 from the storage device 8, and controls the operation of the slave arm 1 in the automatic mode. Moreover, when the manual mode is selected, the control unit 6 controls the operation of the slave arm 1 in the manual mode. Alternatively, when the correctable automatic mode is selected, the control unit 6 controls the operation of the slave arm 1 in the correctable automatic mode.

Moreover, in the above, when either one of the manual mode and the correctable automatic mode is selected, the control unit 6 causes the display device 41 to display and output the situation information of the slave arm 1 throughout the process. As described above, the control unit 6 advances the work process as required in accordance with the operation sequence.

[Entering-Person Sensing Device 93]

The entering-person sensing device 93 is a device which detects an entering person including the operator, who enters into the operational area of the slave arm 1. In this embodiment, the entering-person sensing device 93 is comprised of a light curtain 93A. Note that the entering-person sensing device 93 is not limited to the light curtain 93A, but it may be comprised of, for example, a plurality of camera devices 51 which image the operational area of the slave arm 1, and an image analyzing device (not illustrated) which analyzes the images captured by the camera devices 51 to detect the entering person.

As illustrated in FIG. 1, the operational area of the slave arm 1 is enclosed by a safety fence 90. The safety fence 90 is comprised of a fence 91 which surrounds the operational area of the slave arm 1 from three directions of the four-direction perimeter, and the light curtain 93A which surrounds the remaining one direction of the four-direction perimeter of the operational area of the slave arm 1. Note that the safety fence 90 may be formed by light curtains at the four directions of the perimeter of the operational area of the slave arm 1. The entering person is able to cross the light curtain 93A to enter into the operational area of the slave arm 1.

The light curtain 93A includes a light-emitting part 931 and a light-receiving part 932. Light emitted from the light-emitting part 931 is received by the light-receiving part 932. The light-receiving part 932 detects a passage of an object based on that the light is not received, i.e., the light is interrupted by the object which passes through the light curtain 93A. The light curtain 93A is communicatably connected with the operation regulating device 95 by wiredly or wirelessly. The light curtain 93A outputs an entering-person detection signal to the operation regulating device 95, when the passage of the object is detected.

Note that, in this embodiment, although the area enclosed by the safety fence 90 is defined as the operational area of the slave arm 1, the operational area of the slave arm 1 may be a smaller area. For example, an area obtained by adding an area where the end effector 12 and the workpiece are reachable to a movable area or the workspace of the slave arm 1 may be defined as the operational area of the slave arm 1. Alternatively, a restricted area or an operating area of the slave arm 1 may be defined as the operational area of the slave arm 1. As described above, when the operational area of the slave arm 1 is defined smaller than the area enclosed by the safety fence 90, the light curtains surrounding the perimeter of the operational area, camera(s) which monitors the operational area, piezo-electric sensors which are laid in the operational area, etc. may be utilized as the entering-person sensing device 93.

[Entering-Person Identifying Information Acquisition Device 94]

The entering-person identifying information acquisition device 94 is to acquire entering-person identifying information for identifying whether the entering person into the operational area of the slave arm 1 is the operator who carries the master device 20. The entering-person identifying information acquisition device 94 according to this embodiment uses an RFID. The RFID is comprised of a RF tag 941, and a reader 942 which reads information held by the RF tag 941.

The RF tag 941 is provided to the master device 20 (the console 2). The RF tag 941 stores unique ID information. Note that, instead of the RF tag 941, other information media to/from which data in a built-in memory is capable of contactlessly writing and reading may also be used.

The reader 92 is provided near the light curtain 93A. The reader 942 is capable of using electric waves (electromagnetic waves) to contactlessly read the data held by the RF tag 941 provided to the master device 20 which crosses the light curtain 93A. The reader 942 is communicatably connected with the operation regulating device 95 wiredly or wirelessly. The reader 942 outputs the ID information (the entering-person identifying information) read from the RF tag 941 to the operation regulating device 95.

[Operation Regulating Device 95]

The operation regulating device 95 is to control the operation of the slave arm 1 according to a condition, based on the information acquired from the entering-person sensing device 93 and the entering-person identifying information acquisition device 94. The operation regulating device 95 is a so-called computer, and has an arithmetic processing part, such as a CPU, and a memory part, such as a ROM and/or a RAM (none of them is illustrated). Alternatively, the operation regulating device 95 may be comprised of an arithmetic processing part, such as a CPU, and an emergency stop circuit. The operation regulating device 95 is communicatably connected with the control unit 6, the connector 33, the entering-person sensing device 93 and the entering-person identifying information acquisition device 94 wiredly or wirelessly.

The operation regulating device 95 detects that there is the entering person in the operational area of the slave arm 1 (in this embodiment, inside of the safety fence 90) in response to the entering-person detection signal from the entering-person sensing device 93. When the operation regulating device 95 detects that there is the entering person, it operates the entering-person identifying information acquisition device 94 to acquire the entering-person identifying information from the entering-person identifying information acquisition device 94. The operation regulating device 95 determines whether the entering person is the operator based on the acquired entering-person identifying information.

Here, when the reader 942 successfully reads the ID information (the entering-person identifying information) from the RF tag 941, and the ID information matches with ID information on the slave arm 1 (or the master device 20 capable of manipulating the slave arm 1) which is stored beforehand, the operation regulating device 95 determines that the entering person is the operator who carries the master device 20. Moreover, when the reader 942 successfully reads the ID information from the RF tag 941, and the ID information does not match with the ID information on the slave arm 1 (or the master device 20 capable of manipulating the slave arm 1) which is stored beforehand, the operation regulating device 95 determines that the entering person is other than the operator. Moreover, when the reader 942 has not successfully read the ID information over a given period of time, the operation regulating device 95 determines that the entering person is other than the operator.

Then, the operation regulating device 95 performs the following processing according to the condition. The following Table 1 illustrates the subsequent processing to be performed by the operation regulating device 95 for each condition. In Table 1, the row header expresses the entering person ("Operator" And "Other Than Operator") into the operational area of the slave arm 1, and the column header expresses the control mode ("Automatic Mode", "Manual Mode," And "Correctable Automatic Mode") of the slave arm 1, respectively.

TABLE 1

| | Entering Person | |
|---|---|---|
| | Operator | Other Than Operator |
| Automatic Mode | Operation Regulated | Operation Regulated |
| Manual Mode | Operation Continued | Operation Regulated |
| Correctable Automatic Mode | Operation Continued | Operation Regulated |

As illustrated in Table 1, when the slave arm 1 is in the automatic mode, the operation of the slave arm 1 is regulated even if the entering person is the operator or other than the operator. Here, the operation regulating device 95 outputs an emergency stop signal to the connector 33 to make the connector 33 into the supply interception state. As a result, the power supply from the power source 32 to the motor controller 16 can be stopped to carry out the emergency stop of the slave arm 1. Note that, although the operation regulating device 95 according to this embodiment implements the regulation of the operation of the slave arm 1 by the emergency stop, the mode of the operational regulation is not limited to this configuration. The operational regulation of the slave arm 1 may be implemented by any one of a deceleration of operation, a stop of operation (i.e., the speed of operation is zero), and the emergency stop, which are set beforehand in the operation regulating device 95. Alternatively, the operation regulating device 95 automatically selects the mode of operational regulation from the plurality of modes described above based on a plurality of information, such as the control mode of the slave arm 1, and the situation information acquired from the situation acquisition device 5. When decelerating the operation of the slave arm 1 or stopping the operation, the operation regulating device 95 outputs an instruction to the control unit 6 so that the operation of the slave arm 1 is decelerated or stopped.

Moreover, while the slave arm 1 is in the manual mode or the correctable automatic mode, the operation of the slave arm 1 is continued when the entering person is the operator, and the operation of the slave arm 1 is regulated when the entering person is other than the operator. Here, the operation regulating device 95 processes to perform the emergency stop of the slave arm 1, similar to the above, when regulating the operation of the slave arm 1. Moreover, when the operation of the slave arm 1 is to be continued, the operation regulating device 95 does not perform the processing but continues the monitoring of the entering person into the operational area of the slave arm 1. Note that, when the operation of the slave arm 1 is to be continued, the operation regulating device 95 may give an instruction to the control unit 6 so that the maximum traveling speed of the hand part of the slave arm 1 is regulated to a safety speed or below (e.g., 250 mm/s or less).

As described above, the industrial remote control robot system 100 according to this embodiment includes the master device 20 which receives the operator's manipulation, the slave arm 1 having the plurality of control modes including the automatic mode in which the slave arm 1 is operated based on the prestored task program and the manual mode in which the slave arm 1 is operated based on the operator's manipulation received by the master device 20, the control unit 6 (the control device) which operates the slave arm 1 in one selected from the plurality of control modes, the entering-person sensing device 93 which detects the entering person into the operational area of the slave arm 1, the entering-person identifying information acquisition device 94 which acquires the entering-person identifying information for identifying whether the entering person is the operator who carries the master device 20, and the operation regulating device 95 which regulates the operation of the slave arm 1 based on the information acquired from the entering-person sensing device 93 and the entering-person identifying information acquisition device 94.

While the slave arm 1 is in the automatic mode, the operation regulating device 95 regulates the operation of the slave arm 1 when the entering person is detected, and while the slave arm 1 is in the manual mode, it allows the operation of the slave arm 1 to continue when the entering person is detected and the entering person is the operator, and it regulates the operation of the slave arm 1 when the entering person is other than the operator.

Further, in the system 100, the plurality of control modes further includes the correctable automatic mode in which the slave arm 1 is operated based on the task program while the operation is corrected as required by the operator's manipulation received by the master device 20. While the slave arm 1 is in the correctable automatic mode, the operation regulating device 95 allows the operation of the slave arm 1 to continue when the entering person is detected and the entering person is the operator, and it regulates the operation of the slave arm 1 when the entering person is other than the operator.

According to the remote control robot system 100 described above, the slave arm 1 continues its operation even when the operator who carries the master device 20 enters into the operational area of the slave arm 1. Therefore, the operator is able to manipulate the master device 20 in the operational area of the slave arm 1. Normally, since the operator who carries the master device 20 operates the master device 20 while monitoring the motion of the slave arm 1, he/she can predict the motion of the slave arm 1, and operate the master device 20 to avoid a collision with the slave arm 1. Therefore, the safety of the operator who carries the master device 20 is secured.

Further, in the remote control robot system 100 described above, when the slave arm 1 operates in the automatic mode, the operation of the slave arm 1 is regulated for any entering person into the operational area of the slave arm 1. Therefore, the collision of the entering person into the operational area with the slave arm 1 is prevented.

In addition, in the remote control robot system 100 described above, the operator is able to select the control mode of the slave arm 1 from the automatic mode, the manual mode, and the correctable automatic mode, according to the contents of work or the situation of the slave arm 1. The selection of control mode may be performed based on the operator's judgment. For example, works, such as gripping of a vulnerable component, precise fitting, exact positioning and axial alignment, are preferably be performed in the manual mode or the correctable automatic mode in which the operator's manipulation is capable of being reflected in the motion of the slave arm 1. In such works, for example, if a failure is expected to occur when the slave arm 1 is completely operated automatically, the correctable automatic mode may be selected. Since, in the correctable automatic mode, the automatic operation of the slave arm 1 is the basis of operation while the operation is correctable by the operator's manipulation, the operator's load is smaller as compared with the manual mode and, thus, the lowering of the work efficiency can be controlled. Thus, according to this system 100, by the operator selecting the suitable control mode according to the situation from the plurality of control modes for each work, the non-stopping robot system is implementable.

Moreover, in the industrial remote control robot system 100 described above, the entering-person identifying information acquisition device 94 includes the RF tag 941 provided to the master device 20, and the reader 942 which reads the information on the RF tag 941 and outputs it to the operation regulating device 95.

Thus, the entering-person identifying information is sent to the operation regulating device 95 without the operator who carries the master device 20 performing any special operation so that the operation regulating device 95 automatically performs the processing for identifying the entering person.

Although the suitable embodiment of the present disclosure is described above, the above configuration may be changed as follows, for example.

Figure 4:
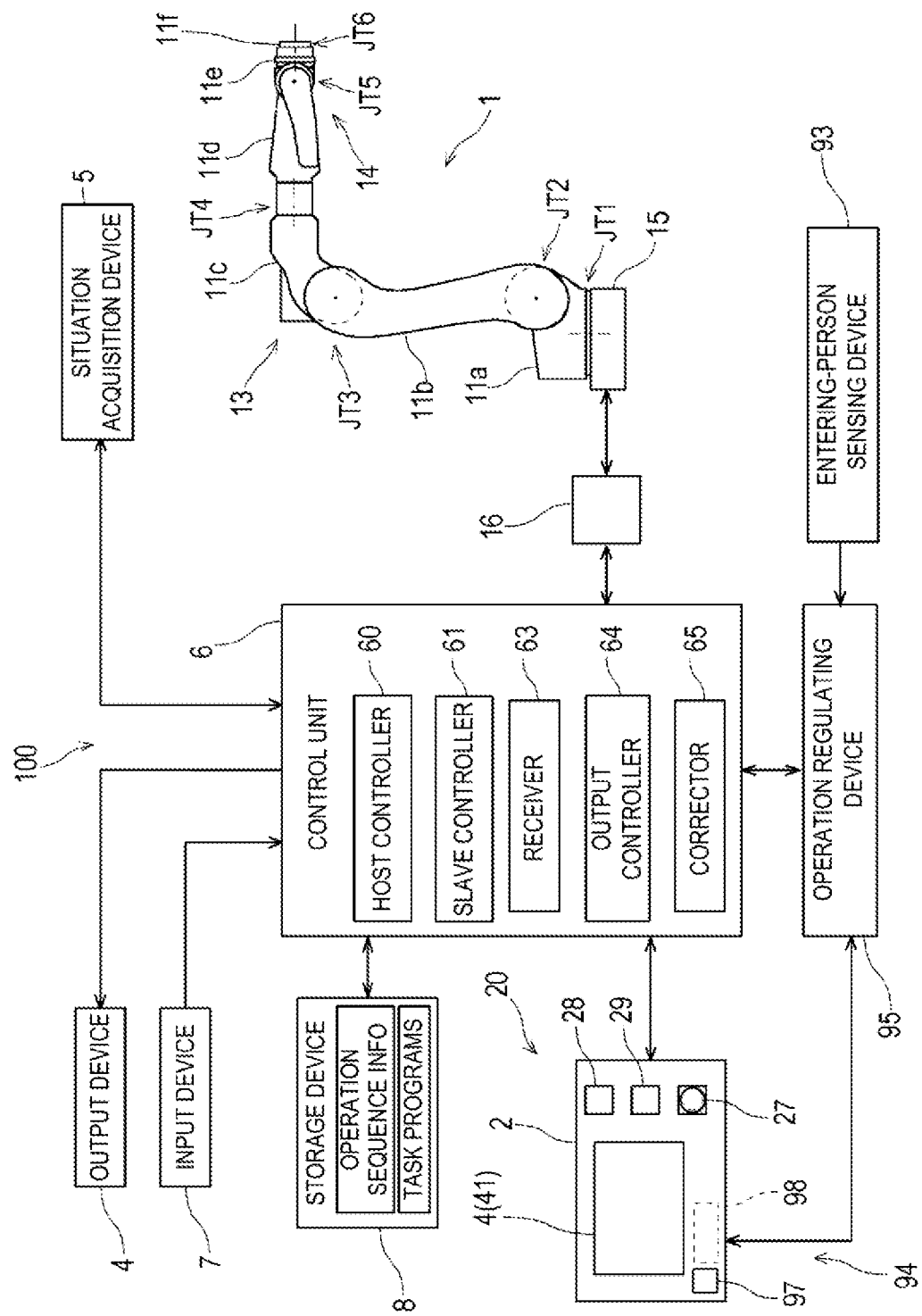
FIG. 4 is a block diagram illustrating a configuration of a control system of a remote control robot system provided with an entering-person identifying information acquisition device according to a modification.

For example, in the embodiment described above, although the RFID is used as the entering-person identifying information acquisition device 94, the entering-person identifying information acquisition device 94 is not limited to this configuration. For example, as illustrated in FIG. 4, the entering-person identifying information acquisition device 94 may be comprised of an identification button 97 provided to the console 2 which is the master device 20, and an identifying information output device 98 which transmits and outputs to the operation regulating device 95 the ID information (the entering-person identifying information) on the master device 20 from the console 2 when the identification button is pushed. Here, the operation regulating device 95 receives the entering-person identifying information from the identifying information output device 98, and compares it with the prestored ID information on the slave arm 1 (or the master device 20 which is capable of manipulating the slave arm 1) to determine whether the entering person is the operator or other than the operator.

In the modification described above, the entering-person identifying information acquisition device 94 includes the identification button 97 provided to the master device 20, and the identifying information output device 98 which outputs the identifying information on the master device 20 to the operation regulating device 95 when the identification button 97 is operated.

Thus, the entering-person identifying information acquisition device 94 can be simply configured, and the operator can intentionally give the entering-person identifying information to the operation regulating device 95.

It is apparent for a person skilled in the art that many improvements and other embodiments of the present disclosure are possible from the above description. Therefore, the above description is to be interpreted only as illustration, and it is provided in order to teach a person skilled in the art the best mode which implements the present disclosure. Details of the structures and/or functions may substantially be changed without departing from the spirit of the present disclosure.

DESCRIPTION OF REFERENCE CHARACTERS

1: Slave Arm
2: Console
4: Output Device
5: Situation Acquisition Device
6: Control Unit
7: Input Device
8: Storage Device
11a-11f: Link
15: Pedestal
16: Motor Controller
20: Master Device
27: Joystick
28: Emergency Stop Button
29: Control Mode Changeover Switch
41: Display Device
60: Host Controller
61: Slave Controller
63: Receiver
64: Output Controller
65: Corrector
90: Safety Fence
93: Entering-person Sensing Device
93A: Light Curtain
94: Entering-person Identifying Information Acquisition Device
941: RF Tag
942: Reader
95: Operation Regulating Device
97: Identification Button
98: Identifying Information Output Device
100: Remote Control Robot System

What is claimed is:

1. A remote control robot system, comprising:
a master device configured to receive manipulation of an operator;
a slave arm having a plurality of control modes including an automatic mode in which the slave arm is operated based on a prestored task program, and a manual mode in which the slave arm is operated based on the manipulation of the operator received by the master device;
a control device configured to operate the slave arm in a selected mode from the plurality of control modes;
an entering-person sensing device configured to detect an entering person into an operational area of the slave arm;
an entering-person identifying information acquisition device configured to acquire entering-person identifying information for identifying whether the entering person is the operator who carries the master device; and
an operation regulating device configured to regulate an operation of the slave arm based on the information acquired from the entering-person sensing device and the entering-person identifying information acquisition device, wherein:
while the slave arm is in the automatic mode, the operation regulating device decelerates or stops the operation of the slave arm when the entering person is detected, and
while the slave arm is in the manual mode, the operation regulating device: (i) allows the operation of the slave arm to continue according to the manipulation that is received by the master device without decelerating the operation of the slave arm when the entering person is detected and the entering person is the operator, and (ii) decelerates or stops the operation of the slave arm when the entering person is other than the operator.

2. The remote control robot system of claim 1, wherein the plurality of control modes further includes a correctable automatic mode in which the slave arm is operated based on the task program, while the operation is corrected as required by the manipulation of the operator received by the master device, and
while the slave arm is in the correctable automatic mode, the operation regulating device allows the operation of the slave arm to continue according to the manipulation that is received by the master device when the entering person is detected and the entering person is the operator, and decelerates or stops the operation of the slave arm when the entering person is other than the operator.

3. The remote control robot system of claim 1, wherein the entering-person identifying information acquisition device includes a Radio Frequency (RF) tag provided to the master device, and a reader configured to read information on the RF tag and output the information to the operation regulating device.

4. The remote control robot system of claim 1, wherein the entering-person identifying information acquisition device includes an identification button provided to the master device, and an identifying information output device configured to output identifying information on the master device to the operation regulating device when the identification button is operated.

5. A remote control robot system, comprising:
a console configured to receive manipulation of an operator;
a slave arm having a plurality of control modes including an automatic mode in which the slave arm is operated based on a prestored task program, and a manual mode in which the slave arm is operated based on the manipulation of the operator received by the console;
a first processor configured to operate the slave arm in a selected mode from the plurality of control modes;
a light curtain or camera configured to detect an entering person into an operational area of the slave arm;
a Radio Frequency Identification Device (RFID) reader configured to acquire entering-person identifying information for identifying whether the entering person is the operator who carries the console; and
a second processor configured to regulate an operation of the slave arm based on the information acquired from the light curtain or camera and the RFID reader, wherein:
while the slave arm is in the automatic mode, the second processor decelerates or stops the operation of the slave arm when the entering person is detected, and
while the slave arm is in the manual mode, the second processor: (i) allows the operation of the slave arm to continue according to the manipulation that is received by the console without decelerating the operation of the slave arm when the entering person is detected and the entering person is the operator, and (ii) decelerates or stops the operation of the slave arm when the entering person is other than the operator.

6. The remote control robot system of claim 5, wherein the plurality of control modes further includes a correctable automatic mode in which the slave arm is operated based on the task program, while the operation is corrected as required by the manipulation of the operator received by the console, and
while the slave arm is in the correctable automatic mode, the second processor allows the operation of the slave arm to continue according to the manipulation that is received by the console when the entering person is detected and the entering person is the operator, and decelerates or stops the operation of the slave arm when the entering person is other than the operator.

7. The remote control robot system of claim 5, wherein a Radio Frequency (RF) tag is provided in the console, and
the RFID reader is configured to read information on the RF tag and output the information to the second processor.

8. The remote control robot system of claim 5, wherein the RFID reader includes an identification button provided to the console, and
the first processor is configured to output identifying information on the console to the second processor when the identification button is operated.

* * * * *